(12) United States Patent
Rode et al.

(10) Patent No.: US 7,800,757 B2
(45) Date of Patent: Sep. 21, 2010

(54) SYSTEM AND METHOD FOR THE SPECTROSCOPIC DETERMINATION OF THE COMPONENTS AND CONCENTRATIONS OF PUMPABLE ORGANIC COMPOUNDS

(75) Inventors: Michael Rode, Jena (DE); Helga Andree, Kiel (DE); Diane F. Malley, Nanaimo (CA)

(73) Assignees: Carl Zeiss Jena GmbH, Jena (DE); Christian-Albrechts-Universitaet Zu Kiel, Kiel (DE)

( * ) Notice: Subject to any disclaimer, the term of this patent is extended or adjusted under 35 U.S.C. 154(b) by 592 days.

(21) Appl. No.: 10/590,985

(22) PCT Filed: Feb. 22, 2005

(86) PCT No.: PCT/EP2005/001799

§ 371 (c)(1),
(2), (4) Date: Apr. 24, 2007

(87) PCT Pub. No.: WO2005/083386

PCT Pub. Date: Sep. 9, 2005

(65) Prior Publication Data

US 2007/0272004 A1 Nov. 29, 2007

(30) Foreign Application Priority Data

Feb. 27, 2004 (DE) .................. 10 2004 010 217

(51) Int. Cl.
*G01N 21/00* (2006.01)
(52) U.S. Cl. .................. 356/432; 73/64.56; 73/61.55; 73/61.68; 222/52; 222/61; 356/436; 356/441
(58) Field of Classification Search ............... 73/64.56, 73/61.55, 61.59, 61.64, 61.68; 356/432–436, 356/439–441; 222/52–61
See application file for complete search history.

(56) References Cited

U.S. PATENT DOCUMENTS 5,042,293 A * 8/1991 Heyde ................... 73/61.56

(Continued)

FOREIGN PATENT DOCUMENTS

DE 25 40 969 3/1977

(Continued)

OTHER PUBLICATIONS

D.F. Malley, P.D. Martin, and L. Dettman, Analysis of Nutrients in Hog Manure by Field-portable Near-infrared Spectroscopy: Results for the Zeiss Corona Spectrometer, Final Report 3 of 3 to CETAC-West on Manure Demo Project Jul. 2001.

*Primary Examiner*—Gregory J Toatley, Jr.
*Assistant Examiner*—Iyabo S Alli
(74) *Attorney, Agent, or Firm*—Frommer Lawrence & Haug LLP

(57) ABSTRACT

The present invention is directed to a fast, nondestructive measurement method for determining the contents of solid, liquid and/or suspended flowing organic compounds. The arrangement according to the invention comprises a sample vessel, a pump, and a measurement cell which form a unit together with a spectroscopic measurement head. The measurement cell is connected to the pump, which can be regulated to vary the flow rate, and to the sample vessel by a pipe, and the spectroscopic measurement head and the regulatable pump have electrical connections to a controlling and evaluating unit. Due to its compact construction, the solution which makes use of the principle of transflection is also particularly suited to mobile use, for example, to determine the components of liquid manure while the latter is being dispensed. In principle, the solution can be transferred to any applications with suspensions or pumpable, homogeneous and inhomogeneous materials.

23 Claims, 2 Drawing Sheets

U.S. PATENT DOCUMENTS

| | | | |
|---|---|---|---|
| 5,420,432 A | 5/1995 | Manook et al. | |
| 6,263,725 B1 | 7/2001 | Garver et al. | |
| 6,657,718 B1 | 12/2003 | Petersen et al. | |
| 2002/0179493 A1* | 12/2002 | Etter | 208/131 |
| 2009/0269836 A1* | 10/2009 | Ellison et al. | 435/286.5 |

FOREIGN PATENT DOCUMENTS

| | | |
|---|---|---|
| DE | 692 08 465 | 8/1996 |
| DE | 196 21 073 | 11/1997 |
| DE | 694 13 992 | 3/1999 |
| DE | 100 16 023 | 1/2003 |
| DE | 102 27 032 | 11/2003 |
| EP | 0 997 732 | 5/2000 |
| EP | 1 308 709 | 5/2003 |
| JP | 56-155850 | 12/1981 |
| JP | 11-196693 | 7/1999 |
| NL | 1015440 | 12/2001 |

* cited by examiner

SYSTEM AND METHOD FOR THE SPECTROSCOPIC DETERMINATION OF THE COMPONENTS AND CONCENTRATIONS OF PUMPABLE ORGANIC COMPOUNDS

CROSS-REFERENCE TO RELATED APPLICATIONS

This application claims priority of International Application No. PCT/EP2005/001799, filed Feb. 22, 2005 and German Application No. 10 2004 010 217.1, filed Feb. 27, 2004, the complete disclosures of which are hereby incorporated by reference.

BACKGROUND OF THE INVENTION a) Field of the Invention

The present invention is directed to a fast, nondestructive measurement method for determining the substances contained in solid, liquid and/or suspended flowing organic compounds. The proposed solution is suitable for calibration to a large number of relevant parameters and can be used in all fields, particularly also in a mobile manner.

b) Description of the Related Art

The through-flow measurement cuvette described in DE 100 16 023 C2 is suitable for the combined use of spectroscopy and polarimetry for the simultaneous determination of a plurality of measured quantities in physical-chemical and bio-technical processes. In particular, substances dissolved in flowing media can be detected continuously and without a delay in time and can be quantitatively determined. Wavelengths in the UV region to the NIR region can be used for spectroscopic measurement. The measurement path is located between two rods of glass, or the like, projecting into the measurement cuvette transverse to the flow direction. Depending on the substance to be investigated, the measurement path must be varied by displacing the rods because measurements can only be carried out by transmission. However, this makes it more difficult or impossible to use the through-flow measurement cuvettes for automated, mobile use.

The determination of the contents of liquid manure, for example, with a view to the precise use thereof as organic fertilizer, is particularly important. Heretofore, the applicable guidelines in this case with regard to the maximum amount to be dispensed could be adhered to only with difficulty because an exact determination of the components and concentrations at the moment of dispensing was impossible. It was only possible to monitor adherence to guidelines through soil analyses before or after dispensing.

According to the known prior art, the determination of the contained substances is carried out after taking samples by subsequent wet chemical measurements in the laboratory. This method is time-consuming and requires extensive preparation of samples. The quantity of samples is limited, and the analysis data can be used for controlling and/or regulating processes in a timely manner only to a limited extent if at all. When the measurement is carried out in through-flow cells with conventional sensors, only the contents that are measurable selectively by the respective sensors can be detected.

A project ("Analysis of Nutrients in Hog Manure by Field-portable Near-infrared Spectroscopy", July 2001) conducted by PDK Projects, Inc., documents the use of NIR spectroscopy for determining components and concentrations of organic waste. However, the results of this project relate only to the use of spectroscopic measuring instruments under laboratory use. The samples to be determined were placed on the spectroscopic measurement head for this purpose. A compact solution for a possible mobile use on a vehicle for dispensing liquid manure was not the aim of the project.

OBJECT AND SUMMARY OF THE INVENTION

It is the primary object of the present invention to develop a fast, nondestructive measurement method and a corresponding arrangement for determining the components of solid, liquid and/or suspended organic waste. The solution is suitable for mobile use, and a high, continuous measurement data density can be realized.

According to the invention, this object is met in an arrangement for the spectroscopic determination of the components and concentrations of pumpable organic waste, comprising a sample vessel, a pump and a measurement cell which form a unit together with a spectroscopic measurement head. The measurement cell is connected to the pump, which can be regulated to vary the flow rate, and to the sample vessel by a pipe. The spectroscopic measurement head and the regulatable pump have electrical connections to a controlling and evaluating unit.

The proposed technical solution delivers representative measurement values of the components of inhomogeneous material using the through-flow method, wherein direct measurement is carried out by light absorption or light transmission. Using the principle of transflection, it is possible to carry out measurements on highly absorbent samples as well as transmissive samples, i.e., also turbid suspensions, and to detect liquid components as well as solid components of the sample.

Due to the compact construction, the solution is also particularly suitable for mobile use for determining the components of solid, liquid and/or suspended organic compounds.

For example, the solution can be used to determine the components of liquid manure and organic fertilizers. By determining the components of the fertilizer in situ, particularly also while it is being dispensed, the fertilizer can be metered in a purposeful manner depending on the directly determined components.

In principle, the proposed technical solution can be transferred to any applications with suspensions or pumpable, homogeneous and inhomogeneous materials. In particular, the invention can conceivably be applied in the foodstuffs industry, sewage control, and process monitoring, e.g., in meat processing and in the production of biogas.

The invention will be described more fully in the following with reference to an embodiment example.

DESCRIPTION OF THE PREFERRED EMBODIMENTS

Figure 1:
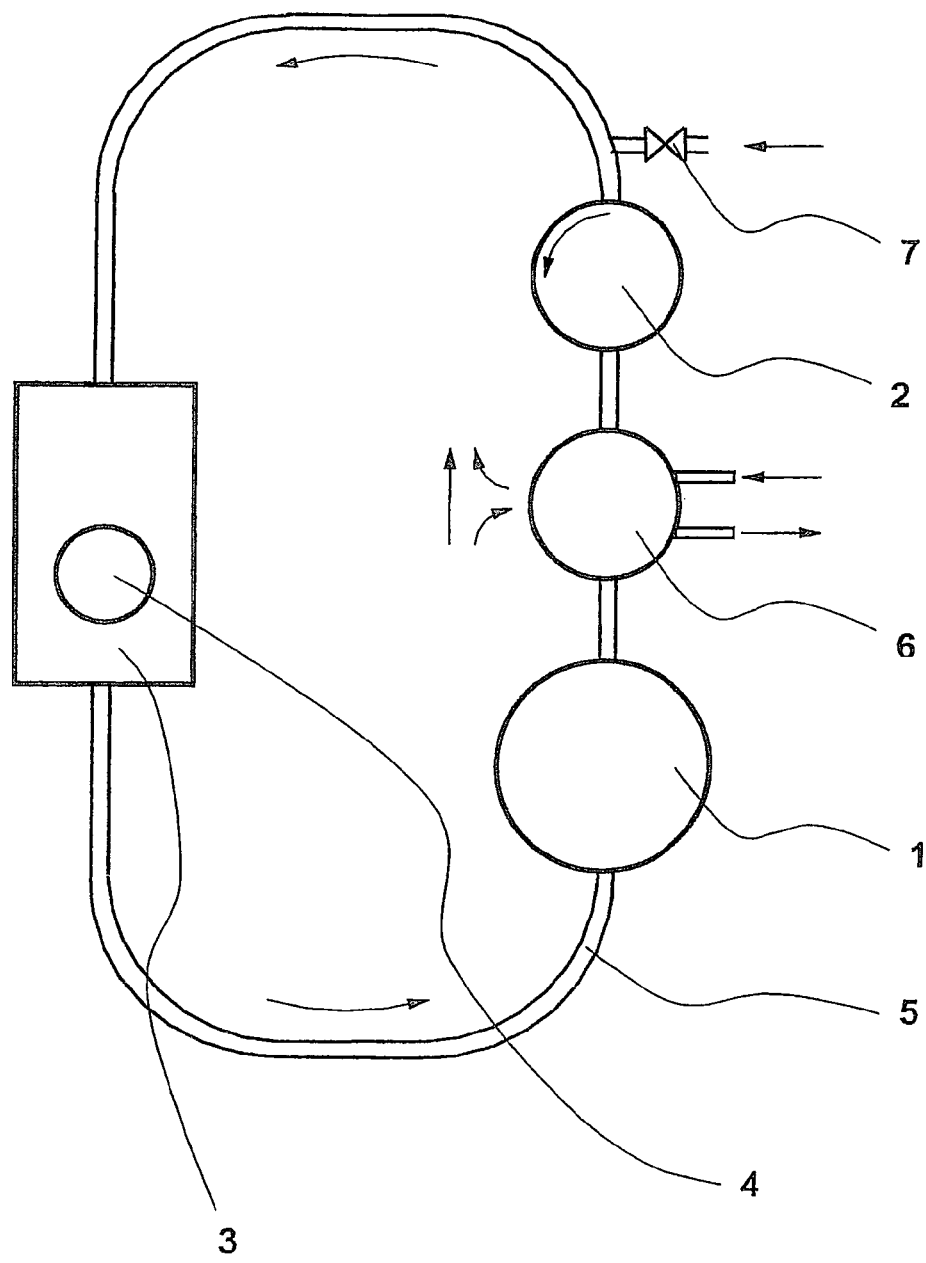
FIG. 1 shows a schematic diagram of the arrangement according to the invention for use in the laboratory.

FIG. 1 shows the arrangement according to the invention for spectroscopic determination of the components and concentrations of pumpable organic compounds. The arrangement comprises a sample vessel 1, a pump 2, and a measurement cell 3 which, together with a spectroscopic measurement head 4, form a unit. The measurement cell 3 is connected to the pump 2, which can be regulated to vary the flow rate, and to the sample vessel 1 by a pipe 5. The spectroscopic measurement head 4 and the regulatable pump 2 have electrical connections to a controlling and evaluating unit (not shown).

The measurement cell 3 is preferably constructed in such a way that the sample flows between two windows which are integrated in the measurement cell opposite one another and perpendicular to the direction of flow. As the sample flows through the measurement cell 3, it must be ensured that no sedimentation, foaming or clogging occurs. The optimal flow rate varies depending on the type of sample as a function of solids content, particle size, particle structure, and thixotropy.

In order to clean the measurement cell 3 of residues from the measured sample and prepare it for the next sample, a multi-port valve 6 is provided which produces connections to a water vessel and/or a vessel with cleaning liquid. The multi-port valve 6 has an actuating drive which is connected to the controlling and evaluating unit. By means of this multi-port valve 6, the measurement cell can be additionally connected to vessels containing test liquids for self-calibration of the measurement arrangement.

The cleaning liquid and rinsing water can be expelled via the multi-port valve 6 after rinsing the measurement cell 3. A repeated rinsing of the measurement cell 3 is advantageous.

The degree of contamination and any cleaning of the measurement cell 3 that may be necessary can be determined by a spectroscopic measurement of the measurement cell 3 without the sample.

Further, the arrangement can have a device for drying the measurement cell 3, which device is likewise connected to the controlling and evaluating unit. Drying is carried out, for example, by aeration in that air is pressed through the measurement cell 3 by means of a valve 7. The air can also be expelled via the multi-port valve 6 after flowing through the measurement cell 3.

Since it must be assumed that the measurement results are affected by temperature, a device for maintaining the temperature of the sample is provided, preferably in or in front of the measurement cell 3.

In an advantageous development, the arrangement is mounted on a vehicle particularly for dispensing pumpable organic waste.

Figure 2:
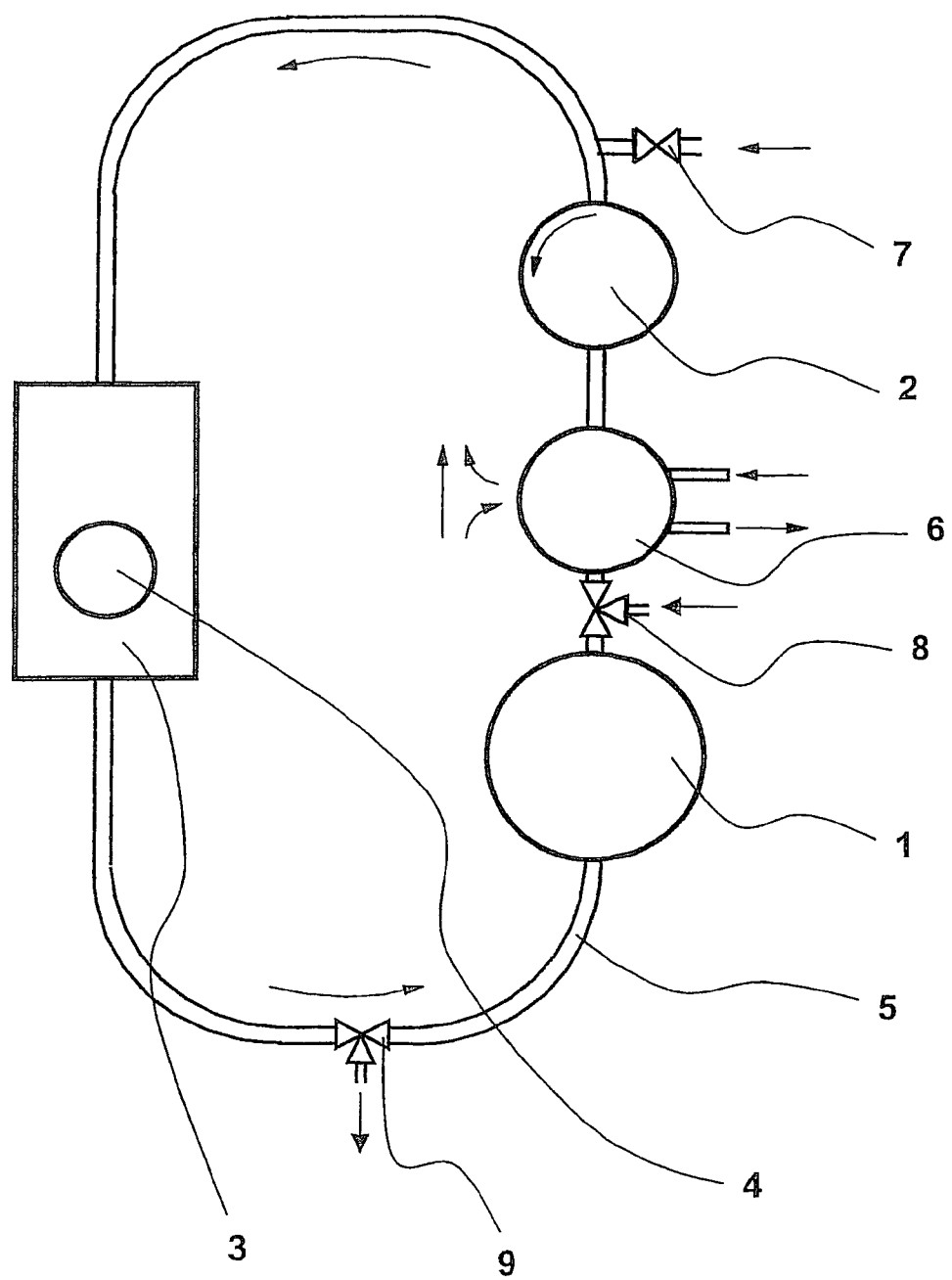
FIG. 2 shows an arrangement which is adapted for mobile use in a vehicle.

FIG. 2 shows an arrangement which is adapted for this purpose for mobile use on a vehicle. To this end, two additional three-way directional valves 8 and 9 are arranged in the pipe 5. In order to determine the components and concentrations while dispensing, a sample is taken from the outlet line of the tank by means of the three-way directional valve 8, pumped through the measurement cell 3, and guided back into the outlet line of the tank by the three-way directional valves 9. The three-way directional valves 8 and 9 preferably likewise have actuating drives which are connected to the controlling and evaluating unit. The sample vessel 1 can remain in the arrangement during this period so that a closed circuit is provided for the rinsing and/or drying process.

The flow volume of an output valve provided at the tank can be regulated by the controlling and evaluating unit by evaluating the determined components and concentrations of the pumpable organic waste. In addition to the determined components and concentrations of substances contained in the sample, previously determined soil values and the instantaneous speed of the vehicle can also be taken into account by the controlling and evaluating unit to generate a suitable control signal for regulating the flow through an outlet valve while dispensing pumpable organic waste. In this way, fertilization can be carried out corresponding to the requirements of the soil.

Since the particle size of organic waste varies sharply and in some cases can lead to clogging, a cutting mechanism and/or sieve are/is advisably arranged in front of the pump 2. Particles which are too large can be made smaller in this way without changing the composition of the sample.

Determining the components of liquid manure is particularly important, for example, with a view to a precise use as organic fertilizer. In order to adhere to the applicable guidelines, it is useful to document the output amount of organic waste with respect to the components and concentrations of individual ingredients. In this way, it is easy to verify the amount of organic waste that has been dispensed.

In the method according to the invention for the spectroscopic determination of the components and concentrations of pumpable organic waste, the sample contained in a sample vessel 1 is pumped by a pump 2 through a measurement cell 3 which forms a unit with the spectroscopic measurement head 4. The measurement head 4 carries out a spectroscopic measurement of the sample flowing through the measurement cell 3 by transmission and/or reflection and conveys the measurement results for further processing to a controlling and evaluating unit. This controlling and evaluating unit determines components and concentrations of substances contained in the sample based on stored specific calibrations. Temperature-dependent, flow-dependent and sample-dependent specific calibrations are required for this purpose.

The measurement cell 3 is preferably constructed in such a way that the sample flows between two windows which are integrated opposite one another in the measurement cell perpendicular to the flow direction. The pump 2 can be regulated for adjusting the flow rate of the sample required for the spectroscopic measurement. In this way, it can be ensured that no sedimentation, foaming or clogging occurs as the sample passes through the measurement cell 3. The optimal flow rate varies depending on the type of sample as a function of solids content, particle size, particle structure, and thixotropy.

To prevent corruption of measurement values, the measurement cell 3 is cleaned after measuring a sample. For this purpose, an existing water vessel is connected to the measurement cell 3 by a multi-port valve 6 in order to remove residues of the measured sample. However, it is also possible to provide an additional vessel with cleaning liquid which is connected to the measurement cell 3 by the multi-port valve 6. After cleaning, the measurement cell 3 is rinsed with water. In some cases, drying of the measurement cell 3 is required after cleaning and rinsing. The drying is carried out by aeration in that air is pressed through the measurement cell 3 by means of a valve 7.

To prevent the influence of temperature on the measurement results, the samples can be temperature-controlled prior to the measurement process by means of a device. This should preferably be carried out in or in front of the measurement cell 3.

In an advantageous construction, the described method can be applied to a vehicle, particularly for dispensing pumpable organic waste. Based on the determined components and concentrations of substances contained in the sample, an additional signal is generated by the controlling and evaluating unit for regulating the flow through an outlet valve while dispensing pumpable organic waste.

In a particularly advantageous solution, previously determined soil values and the instantaneous speed of the vehicle are taken into account by the controlling and evaluating unit in addition to the determined components and concentrations of substances contained in the sample in order to generate a control signal for regulating the flow through an outlet valve when dispensing pumpable organic waste.

In this way, liquid manure can be dispensed as organic fertilizer in an even more purposeful manner. Purposeful metering is made possible by means of the previously determined soil values particularly while dispensing.

The special advantage of the proposed technical solution consists in that it is possible to carry out determinations of components and concentrations of substances contained in the sample in a stationary manner (at-line from sample vessels) or in a mobile manner (in-line while dispensing organic waste).

Further, spectroscopic measurement according to the principle of transflection is particularly advantageous. In this way, it is possible to carry out a direct measurement of the sample through light absorption and/or light transmission without having to change the measurement construction. Depending on the sample to be measured, specifically the solid, liquid and/or suspended organic waste contained therein, the measurement delivers transmission and/or reflection measurement results.

The process of cleaning, rinsing and drying the measurement cell in order to prepare it for the measurement of other samples can be automated and regulated and monitored by the controlling and evaluating unit. The process of cleaning, rinsing and drying can be monitored by spectroscopy. With reference to existing reference standards, the degree of contamination and the relative humidity of the measurement cell can be determined by the measurement head in connection with the controlling and evaluating unit.

When the "cell dry" state is detected, referencing is carried out through automatic white/black calibration of the spectrometer by means of conventional known reference standards. Referencing of this kind can be carried out periodically or as needed. The degree of contamination of the measurement cell can also be monitored by the system itself.

The solution according to the invention also offers the possibility of self-calibration. After the process of cleaning, rinsing and drying has been regulated and monitored by the controlling and evaluating unit, one or more test liquids of defined composition and known absorption or transmission can also be introduced into the measurement cell by means of the multi-port valve. The spectroscopic signal can be calibrated and adjusted on the basis of this calibration liquid. A consistently high measurement accuracy of the system can be achieved in this way. Also, the test liquids used in this case can be expelled via the multi-port valve 6 after the measurement cell 3 is rinsed out.

Complete partial samples or complete batches can be measured continuously with the solution according to the invention without requiring preprocessing of the samples. The samples are not changed by the measurement process. The solution can be calibrated to a large number of relevant parameters and delivers a fast analysis with high measurement data density. Due to the very compact and robust construction, the solution is particularly suited to mobile use.

The solution is suitable for both in-line and at-line determination of the components of solid, liquid and/or suspended organic waste due to the fast and continuous detection of measurement values.

While the foregoing description and drawings represent the present invention, it will be obvious to those skilled in the art that various changes may be made therein without departing from the true spirit and scope of the present invention.

What is claimed is:

1. An arrangement for spectroscopic determination of components and concentrations of any pumpable material, comprising:
   a sample vessel;
   a pump; and
   a measurement cell with a spectroscopic measurement head which carries out a nondestructive spectroscopic measurement of a sample of the pumpable material by light absorption and/or light transmission;
   wherein said measurement cell is connected to the pump, which can vary the flow rate, and to the sample vessel by a pipe;
   wherein said spectroscopic measurement head and the regulatable pump have electrical connections to a controlling and evaluating unit;
   wherein the through-flow volume of an outlet valve provided in the outlet line of the vessel is regulated by the controlling and evaluating unit; and
   wherein the controlling and evaluating unit determines components and concentrations of substances contained in the sample, and regulates the through-flow of the outlet valve based on the determined components and concentrations of the substances contained in the sample.

2. The arrangement according to claim 1;
   wherein the measurement cell is constructed in such a way that the sample flows between two oppositely located windows which are integrated in the measurement cell perpendicular to the direction of flow.

3. The arrangement according to claim 1;
   wherein a multi-port valve is arranged in the pipe to produce connections to a water vessel and/or cleaning liquid vessel.

4. The arrangement according to claim 1;
   wherein the multi-port valve arranged in the pipe can produce connections to one or more vessels with test liquids for self-calibration.

5. The arrangement according to claim 1;
   wherein the multi-port valve has an actuating drive which is connected to the controlling and evaluating unit.

6. The arrangement according to claim 1;
   wherein a device is provided for drying the measurement cell and is connected to the controlling and evaluating unit.

7. The arrangement according to claim 1;
   wherein a device is provided for regulating the temperature of the sample and is connected to the controlling and evaluating unit.

8. The arrangement according to at claim 1;
   wherein the arrangement is connected to the outlet line of a vessel arranged on a vehicle by two three-way directional valves.

9. A method for the spectroscopic determination of the components and concentrations of any pumpable material, comprising the steps of:
   pumping a sample contained in a sample vessel by a pump through a measurement cell with a spectroscopic measurement head;
   allowing the measurement head to carry out a nondestructive spectroscopic measurement of the sample flowing through the measurement cell by light absorption and/or light transmission using the principle of transflection; and
   conveying the measurement results for further processing to a controlling and evaluating unit which determines components and concentrations of substances contained in the sample based on stored specific calibrations.

10. The method according to claim 9;
wherein the pump is regulated to ensure the flow rate of the sample required for the spectroscopic measurement.

11. The method according to claim 9;
wherein an existing water vessel is connected to the measurement cell by a multi-port valve in order to remove residues of the measured sample from the measurement cell and prepare the measurement cell for the next sample.

12. The method according to claim 9;
wherein an existing water vessel and a vessel with cleaning liquid are connected successively to the measurement cell by a multi-port valve in order to clean out residues of the measured sample from the measurement cell, rinse the measurement cell, and prepare the measurement cell for the next sample.

13. The method according to claim 9;
wherein residual moisture is removed from the measurement cell by a device for drying after the measurement cell has been cleaned.

14. The method according to claim 9;
wherein one or more vessels with test liquids for self-calibration of the arrangement is connected to the measurement cell by a multi-port valve.

15. The method according to claim 9;
wherein the sample is temperature-controlled by a device to prevent the influence of temperature on the measurement results.

16. The method according to claim 9;
wherein the measurement head carries out a spectroscopic measurement of the measurement cell without a sample in order to determine the degree of contamination of the measurement cell.

17. The method according to claim 9;
wherein the cleaning and/or drying of the measurement cell and a possible temperature regulation of the sample are/is controlled by the controlling and evaluating unit.

18. A method comprising the steps of:
pumping a sample to be measured by a pump through a measurement cell which forms a unit with a spectroscopic measurement head;
allowing the measurement head to carry out a spectroscopic measurement of the sample flowing through the measurement cell by transmission and/or reflection; and
conveying the measurement results for further processing to a controlling and evaluating unit which determines components and concentrations of substances contained in the sample based on stored specific calibrations;
wherein said sample to be measured is taken from the outlet line of a vessel; and
wherein a control signal is generated by the controlling and evaluating unit based on the determined components and concentrations of substances contained in the sample, and is used to regulate the flow through an outlet valve of the outlet line of the vessel.

19. The method according to claim 18;
wherein the sample is conveyed back into the outlet line of the vessel after being measured.

20. The method according to claim 18;
wherein previously determined soil values are taken into account by the controlling and evaluating unit in addition to the determined components and concentrations of substances contained in the sample in order to generate a control signal for regulating the flow through an outlet valve while dispensing pumpable organic waste.

21. The arrangement according to claim 1;
wherein the arrangement is mounted in its entirety on a vehicle for dispensing pumpable organic waste.

22. The arrangement according to claim 1, further comprising:
means for conveying the sample back into the outlet line downstream of the measurement cell.

23. The method according to claim 19;
wherein the vessel is arranged on a vehicle.

* * * * *